US005158558A

United States Patent [19]

Melker et al.

[11] Patent Number: 5,158,558

[45] Date of Patent: Oct. 27, 1992

[54] NEEDLE-SHIELDING FLUID TRANSFER DEVICE

[75] Inventors: Richard J. Melker; Gary J. Miller, both of Gainesville, Fla.

[73] Assignee: University of Florida, Gainesville, Fla.

[21] Appl. No.: 510,521

[22] Filed: Apr. 18, 1990

Related U.S. Application Data

[63] Continuation-in-part of Ser. No. 371,377, Jun. 26, 1989, abandoned.

[51] Int. Cl.[5] .................... A61B 19/00

[52] U.S. Cl. .................... 604/411; 604/263; 604/905; 141/21; 141/329

[58] Field of Search .................... 141/21-29, 141/328-329; 604/192, 197, 198, 263, 405, 407, 411, 905

[56] References Cited

U.S. PATENT DOCUMENTS

| | | | |
|---|---|---|---|
| 3,610,297 | 10/1971 | Raaf | 141/27 |
| 3,814,941 | 6/1974 | Czaplinski . | |
| 3,826,261 | 7/1974 | Killinger | 604/414 |
| 3,976,073 | 8/1976 | Quick et al. | 604/414 |
| 3,993,063 | 11/1976 | Larrabee | 604/414 |
| 4,143,428 | 3/1979 | Cohen | 604/407 |
| 4,425,120 | 1/1984 | Sampson . | |
| 4,552,277 | 11/1985 | Richardson et al. | 604/411 |
| 4,564,054 | 1/1986 | Gustavsson . | |
| 4,568,346 | 2/1986 | Van Dijk | 604/414 |
| 4,576,211 | 3/1986 | Valentini et al. . | |
| 4,737,144 | 4/1988 | Choksi . | |
| 4,738,379 | 4/1988 | Takasugi . | |
| 4,738,663 | 4/1988 | Bogan . | |
| 4,752,290 | 6/1988 | Schramm . | |
| 4,768,568 | 9/1988 | Fournier et al. | 604/414 |
| 4,787,429 | 11/1988 | Valentini et al. | 604/411 |
| 4,808,381 | 2/1989 | McGregor et al. . | |
| 4,840,618 | 6/1989 | Marvel . | |
| 4,872,494 | 10/1989 | Coccia | 604/411 |

*Primary Examiner*—Stephen C. Pellegrino
*Assistant Examiner*—Michael Rafa
*Attorney, Agent, or Firm*—Spensley Horn Jubas & Lubitz

[57] ABSTRACT

A needle-shielding fluid transfer device for safely transferring fluid from a needle-bearing medical device to a separate container. The device includes a housing having a passage therethrough. At one end section of the housing, the passage has a relatively large diameter and the housing is adapted to easily accept and hold the needle-bearing medical device from which fluid is to be transferred. At a second end section, the housing is adapted to accept the container into which fluid is to be transferred. When a needle-bearing medical device is inserted into the passage at the first end section of the passage and a container is inserted into the second end section of the housing the needle of the needle-bearing medical device enters the container and fluid may be transferred. In one embodiment, the housing is split into two housing components to form a clamshell-like structure.

27 Claims, 4 Drawing Sheets

FIG. 7
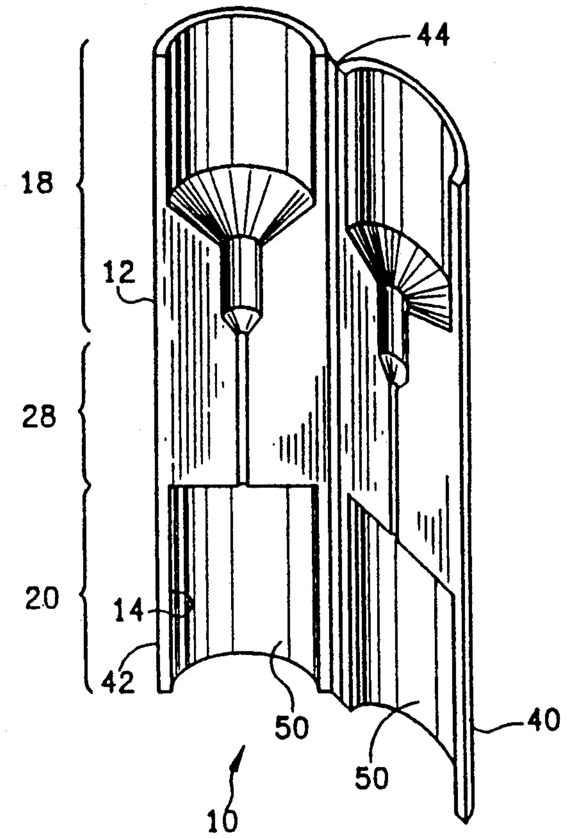
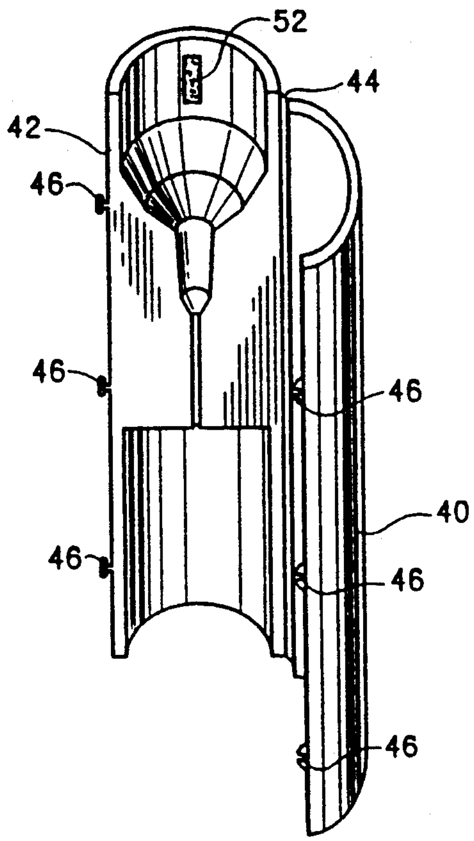
FIG. 8
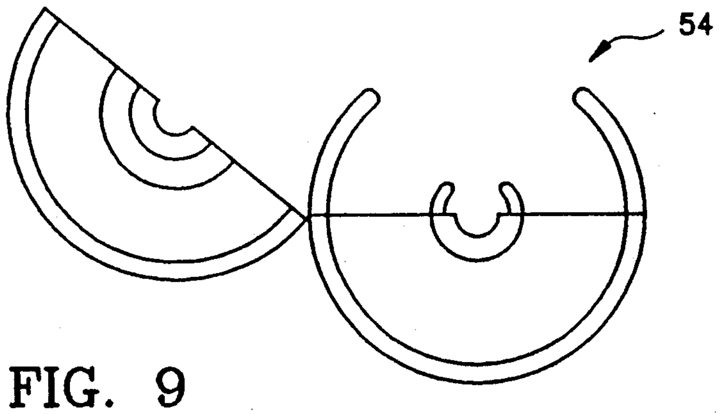
FIG. 9

NEEDLE-SHIELDING FLUID TRANSFER DEVICE

This application is a continuation-in-part of application Ser. No. 07/371,377, filed Jun. 26, 1989, abn. Aug. 8, 1990.

BACKGROUND OF THE INVENTION

1. Field of the Invention This invention relates to safety devices for preventing needle stick injuries to individuals who handle needle-bearing medical devices such as hypodermic syringes. More particularly, the invention relates to devices which shield the needle during the transfer of fluid from a needle-bearing medical device to a separate container and after use of the needle-bearing device.

2. Description of Related Art

Accidental needle sticks with contaminated needles represent a major health problem to hospital and medical facility patients and personnel. It is estimated that there are 800,000 needle sticks per year in the United States resulting in a cost of testing and care of approximately $500,000,000. While needle sticks have been a problem since the invention of hypodermic needles, the recognition of the transfer of the AIDS virus by needle sticks has amplified concern over this problem. A number of other viral and bacterial infections (such as Hepatitis B, tuberculosis, and malaria) can also be transmitted by accidental needle stick injuries.

The technique of drawing blood from patients for evaluation using a needle-bearing medical device (such as a syringe equipped with a hypodermic needle) is particularly likely to result in needle stick injuries to medical personnel since the blood, once drawn into the syringe, must be transferred to separate containers (e.g., evacuated containers) for laboratory analysis. Typically, medical personnel hold an evacuated container in one hand and the fluid-filled needle-bearing medical device in the other hand. The contaminated needle of the needle-bearing device must then be directed toward the rubber cap typically covering the top of the evacuated container. No shield exists between the contaminated needle and the hand holding the container. An improper aim thus easily results in a needle stick by the contaminated needle.

Unprotected needles additionally present a high risk to clean-up personnel and others who may come into contact with the contaminated needle after the used needle-bearing device has been set aside or discarded.

While the problem of needle stick injuries has been recognized in the art, most research for prevention has been focused on the risks associated with recapping and disposal of the needle-bearing device and has been directed towards developing safer needle caps. To date no solution to the danger of unprotected needles during fluid transfer from a needle-bearing medical device to a separate container has been disclosed.

SUMMARY OF THE INVENTION

The present invention provides a fluid transfer device which substantially eliminates the risk of needle stick injuries by contaminated needles. More specifically, the present invention provides a device which shields the needle during the transfer of fluid from a needle-bearing medical device to a separate container, as well as after use of the needle-bearing device.

The fluid transfer device of the present invention includes a housing provided with a passage therethrough. In a first end section of the housing, the passage has a diameter sufficiently large to accept a needle-bearing medical device. In a second end section of the housing, the passage has a diameter sufficiently large to accept a separate container. The length of the housing and its passage are such that when a needle-bearing medical device is inserted into the passage at the first end section of the housing and a separate container is inserted into the passage at the second end section of the housing, the needle penetrates the top of the container.

In one embodiment of the invention, the housing consists of a single piece. In this embodiment, the housing is preferably further provided with an annular ledge positioned to shield the hand of a user of the inventive fluid transfer device during insertion of the needle-bearing medical device into the passage at the first end section of the housing. In another embodiment, the housing is split to form two housing components. The components of this embodiment are coupled together along their mating longitudinal edges but may be uncoupled along at least one longitudinal edge to allow separation of the components to open the housing. In yet another embodiment, the first end section and a middle section of the housing are each split, while the second end section is formed of a single piece. This embodiment is particularly suitable for use with "butterfly-type" needles.

The housing is adapted to retain the needle-bearing medical device once it has been inserted into the passage. For example, in one embodiment of the invention, the needle-bearing medical device is held in the housing by the shape of the first end section. In alternate embodiments, the needle-bearing medical device is held in the passage by protrusions or by adhesive material provided in the housing.

The fluid transfer device may be used to substantially prevent the occurrence of needle sticks by contaminated needles to medical personnel transferring fluid and to others exposed to discarded needle-bearing medical devices, as follows:

Fluid to be transferred (e.g., a patient's blood) is drawn into a needle-bearing medical device (e.g., a syringe equipped with a hypodermic needle). The needle end of the needle-bearing medical device is then inserted into the relatively large passage in the first end section of the housing whereby the annular ledge shields the hand of the person holding the transfer device from the needle and the needle-bearing medical device is pushed into the passage until it becomes securely lodged therein. Alternatively, in the embodiments wherein the housing is split, the housing is opened and the needle-bearing device is placed down into the first end section of one component. The housing components are then closed and coupled together. With these split housing embodiments, the user's hands are not exposed to the needle, since the user need never direct the needle of the needle-bearing device toward them.

Next, a separate container (e.g., an evacuated container) is inserted into the passage in the second end section of the housing whereby the needle penetrates the top of the container. Alternatively, in the unitary housing embodiments, the container may be inserted into the second end section before the needle-bearing device is inserted into the first end section. Fluid from the needle-bearing medical device is then transferred into the container. After fluid has been transferred into the container, the container is removed. Additional containers may then be inserted until all fluid in the needle-bearing medical device has been transferred. Following transfer of the fluid, the needle-bearing medical device and fluid transfer device may be set aside or, preferably, discarded while the needle-bearing medical device is held in the transfer device.

Use of the inventive fluid transfer device permits the needle to remain safely shielded during and after fluid transfer from a needle-bearing medical device. The risk to medical and clean-up personnel of needle sticks by contaminated needles is thus substantially eliminated.

BRIEF DESCRIPTION OF THE DRAWINGS

FIG. 7 is a perspective view of yet another embodiment of the invention.

FIG. 8 is another perspective view of the embodiment of the invention depicted in FIG. 7.

FIG. 9 is a top view showing the first end section of yet another embodiment of the invention.

Like reference characters in the various drawings refer to like elements.

DETAILED DESCRIPTION OF THE INVENTION

The following description is of the best presently contemplated mode of carrying out the invention. This description is made for the purpose of illustrating the general principles of the invention and should not be taken in a limiting sense. The scope of the invention is best determined by reference to the appended claims.

Figure 1:
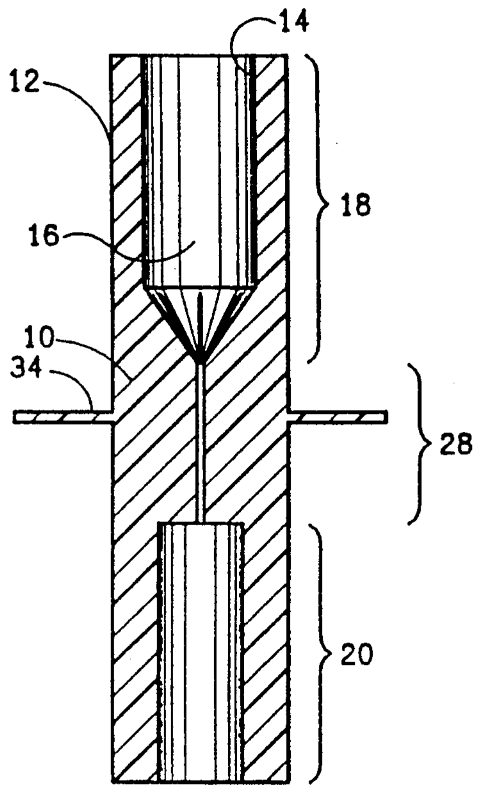
FIG. 1 is a side cross-sectional view of the preferred embodiment of the invention.
Figure 2:
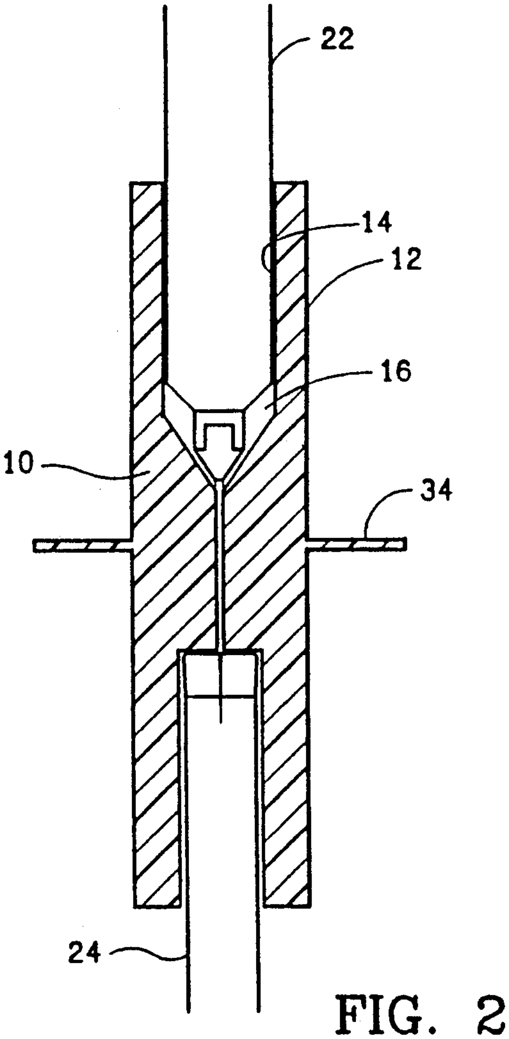
FIG. 2 is a side cross-sectional view of the embodiment of the invention depicted in FIG. 1 with a hypodermic syringe and an evacuated container in place.

Referring now to the drawings, FIGS. 1 and 2 show a first preferred embodiment of the inventive fluid transfer device. The device includes a unitary housing 10 having an outer surface 12 and an inner surface 14. The inner surface 14 defines a passage 16 through the housing 10.

A first end section 18 of the housing 10 is shaped to accept and hold a needle-bearing medical device having a needle and a body component. A second end section 20 of the housing 10 is shaped to accept a separate container. For convenience, the invention will be described hereafter with reference to a syringe equipped with a hypodermic needle (hypodermic syringe 22 shown in FIG. 2) as the needle-bearing medical device, and an evacuated container 24 covered with a self-sealing cover as the separate container. However, the scope of the invention includes needle-bearing medical devices other than hypodermic syringes and containers other than such evacuated containers.

The diameter of the passage at the first end section 18 of the housing 10 is at least sufficiently large to admit a portion of the syringe component of the hypodermic syringe 22 and is preferably in excess of 2 cm. An easy target for an operator's hand guiding the needle of the hypodermic syringe 22 into the passage 16 is thereby provided.

Figure 3:
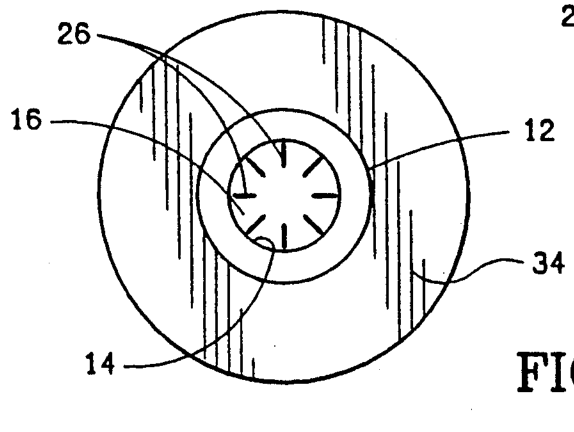
FIG. 3 is a top view of the invention depicted in FIGS. 1 and 2 showing the first end section.

In the first preferred embodiment of the invention, the diameter of the passage 16 in the first end section 18 of the housing 10 is larger than the diameter of the syringe component of the hypodermic syringe 22 from which fluid is to be transferred, and the inner surface 14 of the housing 10 is provided with a plurality of ribs 26 in the first end section 18, as shown in FIG. 3. The ribs 26 are sized to provide a friction fit against the syringe component of the hypodermic syringe 22 to hold the hypodermic syringe 22 when it is inserted into the first end section 18 of the housing 10. Therefore, the size of the ribs 26 depends on the diameter of the passage 16 in the first end section 18 and the size of the hypodermic syringe 22 from which fluid is to be transferred. The ribs 26 may be arranged in any orientation and are preferably made of a slightly resilient material (e.g., a soft plastic) so that the first end section 18 may accommodate and hold syringes of slightly varying dimensions (e.g., 10 and 12 cc capacity syringes).

Alternative means of holding the hypodermic syringe 22 may be used in lieu of the ribs 26. For example, the diameter of the passage in the first section 18 of the housing 10 may be such that when a hypodermic syringe 22 of a predetermined size is inserted, the inner surface 14 of the housing 10 defining the first end section 18, provides a friction fit against the syringe component and the hypodermic syringe 22 is thereby held.

In the first preferred embodiment, the housing 10 is further provided with a middle section 28 wherein passage 16 is narrowed. Middle section 28 is bordered on one end by the first end section 18 and on the other end by the second end section 20. In the middle section 28, the passage 16 has a diameter sufficient to admit the needle of the hypodermic syringe 22 (e.g., sufficient to hold needles of 19 gauge), but insufficient to admit the syringe component of the hypodermic syringe 22 or the evacuated container 24. The middle section 28 is of a length slightly shorter than the length of the needle of the hypodermic syringe 22 from which fluid is to be transferred. A sufficient length of the needle will therefore penetrate the cover of the evacuated container inserted into the second end section 20. Preferably, the middle section 28 is approximately 1 cm shorter than the needle of the hypodermic syringe 22.

Figure 4:
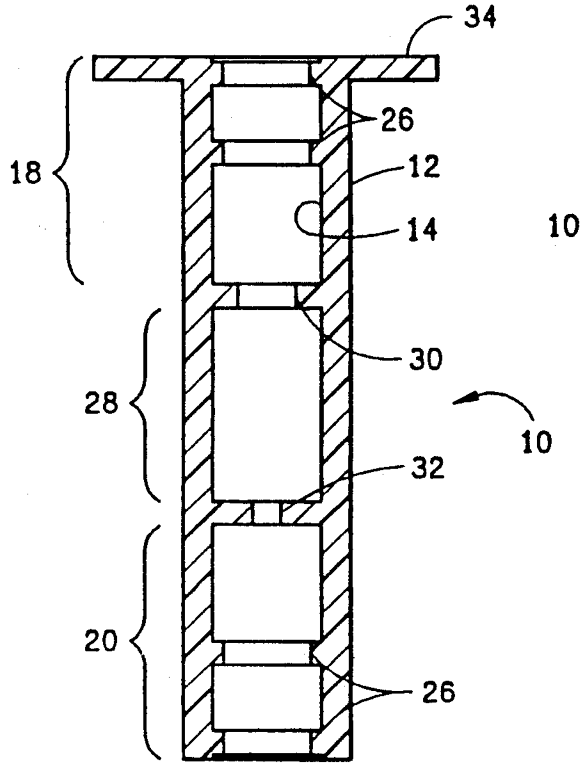
FIG. 4 depicts a cross-sectional slice of another embodiment of the invention.

In an alternate embodiment, depicted in FIG. 4, the passage 16 has a uniform diameter throughout the length of the housing 10. The diameter of the passage 16 is sufficiently large to accept the syringe component of the hypodermic syringe 22 and the container 24. An annular shoulder 30 provided on the interior surface 14 of the housing 10 prevents the syringe 22 from slipping through the housing upon insertion into the passage 16 in the first end section 18. A second annular shoulder 32 may be provided to prevent the container, inserted into the passage 16 in the second end section 20, from slipping too deeply into the passage 16. Alternatively, a plurality of suitably sized protrusions may be provided in lieu of the annular shoulders 30, 32.

As illustrated in FIG. 4, ribs 26 may be arranged in an annular fashion. Furthermore, additional ribs 26 may be provided on the interior surface 14 of the second end section 20 of the housing 10 to hold the container.

In the first preferred embodiment of the invention, the housing 10 further includes at least one annular ledge 34 provided on its outer surface 12. The annular ledge 34 is preferably formed integrally with the housing 10 and is preferably at least 1 cm wide. The size and shape of the annular ledge 34 thus offer additional needle-shielding protection to the hand of an operator of the fluid transfer device. Annular ledge 34 may be of any convenient shape in order to provide needle-shielding protection (e.g., circular or elliptical). The annular ledge 34 may be positioned to maximize protection of the operator's hand. In the illustrated embodiment, it is positioned at approximately the mid-point of the length of the housing 10. In this position, the annular ledge 34 additionally acts as a guard to prevent the operator's hand from slipping towards the first end section 18 of the housing 10 while the hypodermic syringe 22 is being inserted into the passage 16.

Figure 5:
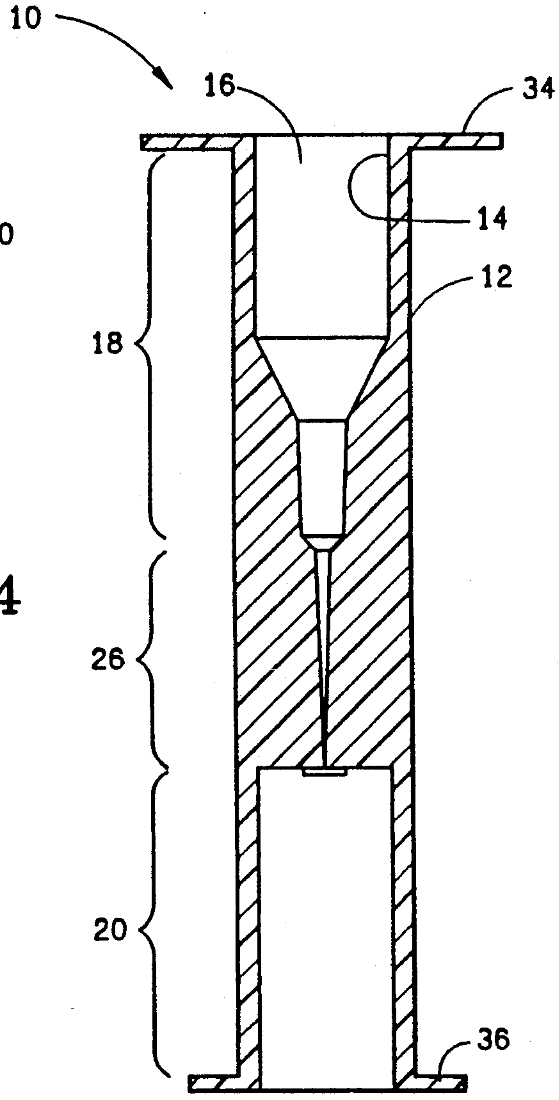
FIG. 5 is a side cross-sectional view of yet another embodiment of the invention.
Figure 6:
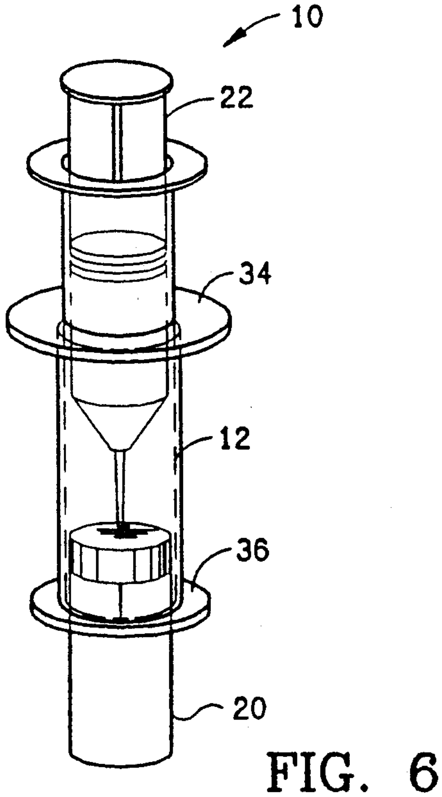
FIG. 6 is a perspective view of the embodiment of the invention depicted in FIG. 5 with a hypodermic syringe and an evacuated container in place.

In another embodiment of the invention, depicted in FIGS. 5 and 6, the housing 10 is provided with two annular ledges 34 and 36, one adjacent each end section of the housing 10.

FIGS. 7 and 8 depict a second preferred embodiment of the invention. In this embodiment, the housing 10 is split to form two mating housing components 40 and 42, each of which comprises approximately half of the housing 10. The housing 10 may be split along its longitudinal axis to form two symmetrical housing halves as depicted. Alternatively, the housing 10 may be split into two components of different sizes. For convenience, the two components 40, 42 will be referred to hereafter as housing halves 40, 42. A thin hinge 44 preferably couples the two housing halves along one mating longitudinal edge of each to form a clamshell-like structure. The other longitudinal edges of the halves are provided with a second coupling mechanism which allows these edges to be separated to open the housing 10 . As depicted in FIG. 8, the second coupling mechanism may consist of small hooks 46 provided along one longitudinal edge of one half 42 and complimentary loops 48 provided along the mating longitudinal edge of the other half 40.

Each housing half 40, 42 is provided with a groove 50. When the two housing halves 40, 42 are coupled together along their respective mating edges, a housing 10 much like that of the first preferred embodiment is formed, i.e., the housing 10 includes outer and inner surfaces 12 and 14, respectively, with the grooves 50 defined by the inner surface 14 forming a passage through the housing 10 when the housing halves are coupled. The housing 10 further includes first and second end sections 18 and 20, respectively, and a middle section 28 with passage 16 passing through each.

The housing 10 of the second preferred embodiment is adapted to retain a needle-bearing medical device in one of the halves 40 or 42 when the housing 10 is open, i.e., when the halves are separated along one of their longitudinal edges. For example, the diameter of groove 50 in the first end section 18 of one of the halves of the housing 10 may be such that when a needle-bearing medical device of a predetermined size is inserted, the inner surface 14 of the housing 10 defining the first end section 18 provides a friction fit against the body component of the needle-bearing medical device and thereby holds it in the half housing. Alternatively, as depicted in FIG. 8, adhesive material 52 may be placed into one half 40 or 42 of the first end section of the housing to retain the needle-bearing medical device therein when the housing is open. Suitable adhesive material includes, for example, a piece of double-sided adhesive tape. Yet another option for retaining the needle-bearing device in one half 40 or 42 when the housing 10 is open is depicted in FIG. 9. In this embodiment, the first end section of one half of the housing is provided with flexible protrusions 54 which lock around the needle-bearing medical device as it is placed into the housing half to retain it therein.

Figure 10:
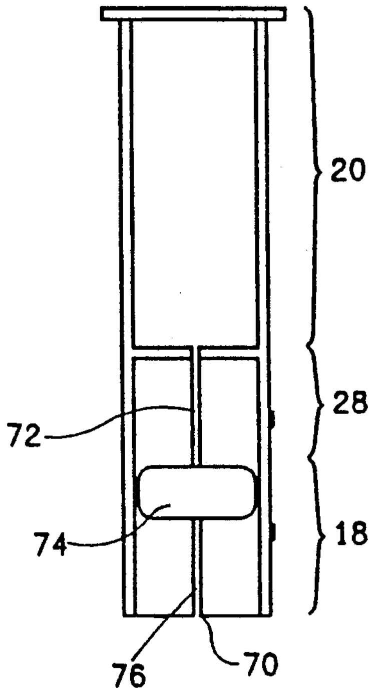
FIG. 10 is a side view of another embodiment of the invention.
Figure 11:
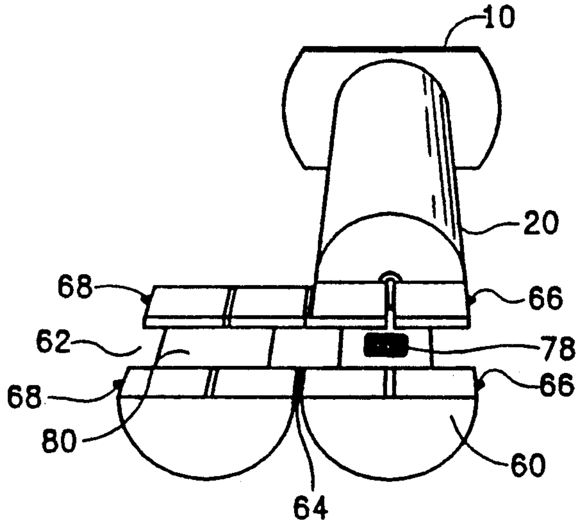
FIG. 11 is a perspective view of an embodiment of the invention depicting the two housing components of the first end section and middle section in the open position.

FIGS. 10 and 11 depict embodiments of the present invention particularly suitable for use with butterfly needles having a needle component connected to a central body component, connected, in turn, to tubing leading to a syringe. In these embodiments, the first end section 18 and the middle section 28 of the housing are split into two halves 60, 62 along the longitudinal axis of the housing 10. The second end section 20 of the housing 10 is formed as a single piece. The two halves 60, 62 are preferably connected along one of their mating edges by a coupling mechanism such as hinges 64, and along the other of their mating edges by a coupling mechanism which allows separation of the halves 60, 62, for example, a complimentary hook 66 and loop 68 arrangement.

In the embodiment depicted in FIG. 10, the halves 60, 62 of the first end and middle sections 18–28 are provided with grooves which form a passage 70 shaped to accommodate the components of a butterfly needle when the two halves are mated in their closed position. Specifically, passage 70 includes a first section 72 shaped to accommodate the needle component of a butterfly needle, a second section 74 shaped to accommodate its central body component ("wings"), and a third section 76 shaped to accommodate its tubing. The grooves of the halves 60, 62 which form the passage 70 may be shaped to hold the butterfly needle in one half by a friction fit when the halves 60, 62 are separated and the first end and middle sections 18–28 are in their open position.

Alternatively, adhesive material such as a piece of double sided tape 78, may be placed in section 74 of the passage 70 to retain the butterfly needle in one half 60 or 62 when the housing is open. The embodiment of the invention depicted in FIG. 11 depicts a further variation in that a portion of the housing 10 forming the first end section is cut-away to form a more narrow section 80 such that the wings of the butterfly needle project beyond the outer walls of the housing 10. The design of this embodiment permits use of a relatively small housing 10 (e.g., sized to accommodate a small evacuated container) for transferring fluid from a butterfly needle having large wings.

The inventive fluid transfer device is preferably made of a suitable, non-toxic plastic (e.g., polytetrafluroethylene) and may be manufactured in a single unit using an injection molding technique. The inventive device may therefore be manufactured at a relatively low cost.

In typical usage of the first preferred embodiment of the fluid transfer device, an operator draws fluid (e.g., blood from the vein or artery of a patient) into a syringe 22 through its hypodermic needle. The syringe 22 with hypodermic needle in place is then inserted into the relatively large opening of the passage 16 in the first end section 18 of the housing 10, whereby the hand of the operator is positioned behind and protected by the annular ledge 34. The syringe 22 is pushed into the passage 16 until its progress is blocked by middle section 28. The needle of the syringe 22 passes through narrowed passage 16 of middle section 28 and protrudes into the second end section 20. An evacuated container 24 is then inserted into the second end section 20 until its progress is blocked by middle section 28, whereby the needle of the hypodermic syringe 22 pierces the self-sealing cap of the evacuated container 24 and fluid drains into the evacuated container 24 until the hypodermic syringe 22 is empty or the container 24 is full. The evacuated container 24 is then removed. A new container may be inserted if fluid remains to be transferred from the hypodermic syringe 22. After all fluid has been removed from the hypodermic syringe 22, the hypodermic syringe 22 and fluid transfer device may be disposed of as a single unit. Thus, the needle of the hypodermic syringe remains shielded even after disposal.

The second preferred embodiment may be used in substantially the same manner with a few modifications. First, the housing 10 is opened by separating the two halves 40, 42 along one of their mated longitudinal edges. The needle-bearing medical device from which fluid is to be transferred is then placed down into one of the halves 40 or 42 to allow the needle component to rest in the middle section 28 and slightly protrude into the second end section 20. The two halves 40 and 42 are then closed around the needle-bearing medical device. Next, an evacuated container is inserted into the second end section 20 to drain the fluid from the needle-bearing medical device. The second preferred embodiment of the invention is particularly safe to use since the needle end of the needle-bearing medical device is never moved toward the hands of a user.

The inventive needle-shielding fluid transfer device, as described above, provides a cost-efficient method of substantially eliminating the risk of needle stick injuries by contaminated needles to medical and clean-up personnel both during and after fluid transfer from a needle-bearing medical device to a separate container.

Several embodiments of the present invention have been described, however, it will be understood that various modifications may be made without departing from the spirit and scope of the invention. For example, the various elements of the device can be made of different materials and in different general shapes. Further, the configurations of the invention shown in FIGS. 7–11 can be made such that the housing components 40, 42 are not symmetric, and/or do not each comprise approximately half of the housing 10. Accordingly, it is to be understood that the invention is not to be limited by the specific illustrated embodiments, but only by the scope of the appended claims.

We claim:

1. A needle-shielding fluid transfer device for transferring fluid from a needle-bearing medical device to at least one separate container, the needle-bearing medical device having a needle and a body component, comprising:

a housing having an interior surface and an exterior surface, the interior surface defining a passage therethrough, the housing further having:

(a) means for accepting the needle-bearing medical device from which fluid is to be transferred;

(b) means for retaining the needle bearing medical device within the housing during and following transfer of fluid from the needle bearing medical device;

(c) means for accepting a container into which fluid is to be transferred; and (d) means for connecting the means for accepting the needle-bearing medical device and the means for accepting a container, whereby when a needle-bearing medical device and a container are inserted into the housing, the needle of the needle-bearing medical device enters the container;

wherein the means for accepting a container has a length sufficient to fully shield the needle of the needle-bearing medical device when the needle-bearing medical device is inserted into the means for accepting the needle bearing medical device and wherein the needle-bearing medical device is retained in the housing by the means for retaining the needle-bearing medical device after the transfer of fluid from the needle-bearing medical device to the container and upon disposal of the needle-bearing medical device.

2. The needle-shielding fluid transfer device of claim 1 wherein the means for accepting the needle-bearing medical device and the means for retaining the needle-bearing medical device comprise a first end section of the housing, the means for accepting a container comprises a second end section of the housing, and the means for connecting comprises a middle section through which the passage connects the first and second end sections.

3. A needle-shielding fluid transfer device for transferring fluid from a needle-bearing medical device to at least one separate container, the needle-bearing medical device having a needle and a body component, comprising:

a housing having an interior surface and an exterior surface, the interior surface defining a passage therethrough, the housing further having:

(a) a first end section adapted to accept and retain a needle-bearing medical device from which fluid is to be transferred during and following transfer of fluid from the needle-bearing medical device;

(b) a second end section adapted to accept a container into which fluid is to be transferred; and (c) a middle section located between the first and second end sections, and through which the passage connects the first and second end sections, the middle section being adapted to admit the needle of the needle-bearing medical device and to prevent the body component of the needle-bearing medical device and the container from entering, and the middle section having a length shorter than the needle of the needle-bearing medical device;

wherein the second end section has a length sufficient to fully shield the needle of the needle-bearing medical device when the needle-bearing medical device is inserted into the first end section and wherein the needle-bearing medical device is retained in the housing after the transfer of fluid from the needle-bearing medical device to the container and upon disposal of the needle-bearing medical device.

4. The needle-shielding fluid transfer device of claim 3, wherein the first end section of the housing is adapted to accept and retain a hypodermic syringe and the second end section is adapted to accept an evacuated container provided with a cover, and wherein when the hypodermic syringe is placed in the first end section of the passage and the evacuated container is placed in the second end section of the passage, the needle of the hypodermic syringe pierces the cover of the evacuated container.

5. The needle-shielding fluid transfer device of claim 3, wherein the diameter of the passage is uniform throughout the housing and wherein the interior surface of the middle section is provided with means for preventing the body component of the needle-bearing medical device and the container from entering into the passage in the middle section.

6. The needle-shielding fluid transfer device of claim 5, wherein the means for preventing the body component of the needle-bearing medical device and the container from entering the passage in the middle section comprises two annular shoulders positioned on the interior surface of the middle section of the housing.

7. The needle-shielding fluid transfer device of claim 3, wherein the diameter of the passage in the middle section is smaller than its diameter in the first and second end sections, the diameter being sufficiently large to admit the needle of the needle-bearing medical device but smaller than the diameter of the body component of the needle-bearing medical device and the diameter of the container.

8. The needle-shielding fluid transfer device of claim 3, wherein the diameter of the passage in the first end section of the housing is larger than the diameter of the body of the needle-bearing medical device and wherein the needle-bearing medical device is retained by a plurality of ribs provided on the inner surface of the housing along the first end section of the housing.

9. The needle-shielding fluid transfer device of claim 8, wherein the ribs are made of a slightly resilient material, whereby needle-bearing medical devices of varying dimensions may be held in the first end section of the housing.

10. The needle-shielding fluid transfer device of claim 3, further comprising means for shielding the hand of an operator from the needle of the hypodermic syringe being inserted into the first end section of the housing.

11. The needle-shielding fluid transfer device of claim 10, wherein the means for shielding comprises at least a first annular ledge positioned on the exterior surface of the housing.

12. The needle-shielding fluid transfer device of claim 11, wherein the first annular ledge is formed integrally with the housing.

13. The needle-shielding fluid transfer device of claim 11, wherein the housing further comprises a second annular ledge, the first annular ledge being positioned adjacent with the first end section of the housing, the second annular ledge being positioned adjacent the second end section of the housing.

14. The needle-shielding fluid transfer device of claim 3 wherein at least the first end section and the middle section of the housing are split to form two housing components and wherein the two housing components are provided with means for coupling the two components along their longitudinal edges.

15. The needle-shielding fluid transfer device of claim 14 wherein the means for coupling the two housing components comprise at least a first hinge connecting a first longitudinal edge of each component.

16. The needle-shielding fluid transfer device of claim 15 wherein the means for coupling further comprises at least a first hook positioned along a second longitudinal edge of one housing component and at least a first complimentary loop positioned along a second longitudinal edge of the other housing component.

17. The needle-shielding fluid transfer device of claim 14 wherein the entire housing is split to form two housing components.

18. The needle-shielding fluid transfer device of claim 14 wherein the inner surface of each housing component at the first end section of the housing conforms approximately to the shape of the needle-bearing medical device and retains the needle-bearing medical device by friction fit when the two housing components are uncoupled along one longitudinal edge each.

19. The needle-shielding fluid transfer device of claim 14 wherein at least one housing component is provided with means for retaining the needle-bearing medical device in the first end section when the two components are uncoupled along one longitudinal edge of each.

20. The needle-shielding fluid transfer device of claim 19 wherein the means for retaining the needle-bearing medical device comprises flexible protrusions which lock around the needle-bearing medical device.

21. The needle-shielding fluid transfer device of claim 19 wherein the means for retaining the needle-bearing medical device comprises means for adhering the needle-bearing medical device to one housing component at the first end section of the housing.

22. The needle-shielding fluid transfer device of claim 21 wherein the means for adhering the needle-bearing medical device comprises double-sided tape.

23. The needle-shielding fluid transfer device of claim 14 wherein the inner surface of each housing component at the first end section and the middle section of the housing conforms approximately to the shape of a butterfly needle.

24. The needle shielding fluid transfer device of claim 14 wherein the housing is split along its longitudinal axis to form two symmetrical housing halves.

25. A method for transferring fluid from a needle-bearing medical device, having a needle and a body component, to a container, comprising the steps of:

(1) providing a fluid transfer device comprising a housing having a passage therethrough, the housing having a first end section adapted to accept and retain a needle-bearing medical device from which fluid is to be transferred during and following transfer of fluid from the needle-bearing medical device, a second opposing end section adapted to hold a container into which fluid from the needle-bearing medical device is to be transferred, and a middle section located between the first and second end sections, and through which the passage connects the first and second end sections, the middle section being adapted to admit the needle of the needle-bearing medical device and to prevent the body component of the needle-bearing medical device to be held by the first end section and the container to be placed into the second end section from entering, the middle section further having a length shorter than the length of the needle of the needle-bearing medical device, and the second end section having a length sufficient to fully shield the needle of the needle-bearing medical device when the needle-bearing medical device is retained in the first end section;

(2) inserting the needle-bearing medical device from which fluid is to be transferred into the first end section of the housing, whereby the needle enters the middle section of the housing and protrudes into the passage in the second end section of the housing and is shielded by the second end section; and (3) inserting the container into which fluid is to be transferred into the second end section of the housing whereby the needle of the needle-bearing medical device enters the container and fluid flows from the needle-bearing medical device into the container.

26. A method for safely transferring blood from a patient into a container for evaluation, the container being equipped with a self-sealing cover, comprising the steps of:

(a) providing a syringe equipped with a hypodermic needle;

(b) inserting the hypodermic needle of the syringe into a patient's vein or artery and drawing a blood sample into the syringe;

(c) removing the hypodermic needle from the patient's vein or artery;

(d) providing a fluid transfer device comprising a housing having a passage therethrough, the housing having a first end section adapted to accept and retain a needle-bearing medical device from which fluid is to be transferred during and following transfer of fluid from the needle-bearing medical device, a second opposing end section adapted to hold a container into which fluid from the needle-bearing medical device is to be transferred, and a middle section located between the first and second end sections, and through which the passage connects the first and second end sections, the middle section being adapted to admit the needle of the needle-bearing medical device and to prevent the body component of the needle-bearing medical device to be held by the first end section and the container to be placed into the second end section from entering, the middle section further having a length shorter than the length of the needle of the needle-bearing medical device, and the second end section having a length sufficient to fully shield the needle of the needle-bearing medical device when the needle-bearing medical device is retained in the first end section;

(e) inserting the syringe into the first end section of the housing, needle first;

(f) inserting the container into which fluid is to be transferred into the second end section of the housing whereby the hypodermic needle pierces the cover of the container and fluid from the syringe is transferred directly into the container until the syringe is empty or the container if filled;

(g) removing the container;

(h) inserting, filling and removing additional containers until all fluid is drained from the syringe; and (i) discarding the syringe while retained in the fluid transfer device.

27. A method for transferring fluid from a needle-bearing medical device, having a needle and a body component, to a container, comprising the steps of:

(a) providing a fluid transfer device comprising a housing having a passage therethrough, the housing being split into two housing components, each housing component including means for coupling to the other housing half along their respective longitudinal edges, the housing having a first end section adapted to accept and retain a needle-bearing medical device from which fluid is to be transferred during and following transfer of fluid from the needle-bearing medical device, a second opposing end section adapted to hold a container into which fluid from the needle-bearing medical device is to be transferred, and a middle section located between the first and second end sections, and through which the passage connects the first and second end sections, the middle section being adapted to admit the needle of the needle-bearing medical device and to prevent the body component of the needle-bearing medical device to be held by the first end section and the container to be placed into the second end section from entering, the middle section further having a length shorter than the length of the needle of the needle-bearing medical device, and the second end section having a length sufficient to fully shield the needle of the needle-bearing medical device when the needle-bearing medical device is retained in the housing;

(b) opening the housing by uncoupling the two housing components of the housing along one of their longitudinal edges;

(c) placing the needle-bearing medical device from which fluid is to be transferred into the first end section of the housing, whereby the needle is placed into the middle section of the housing and protrudes into and is shielded by the second end section of the housing;

(d) closing the housing around the needle-bearing medical device by coupling the uncoupled longitudinal edges of the two halves; and (e) inserting the container into which fluid is to be transferred into the second end section of the housing, whereby the needle of the needle-bearing medical device enters the container and fluid flows from the needle-bearing medical device into the container.

* * * * *